United States Patent [19]

Koehler et al.

[11] Patent Number: 5,231,231
[45] Date of Patent: Jul. 27, 1993

[54] PROCESS FOR PREPARING A POLY(1,4-BUTANEDIOL-ω,ω'-BISMERCAPTAN)

[75] Inventors: Ulrich Koehler, Worms; Hardo Siegel, Speyer; Eckhard Hickmann, Dannstadt-Schauernheim, all of Fed. Rep. of Germany

[73] Assignee: BASF Aktiengesellschaft, Ludwigshafen, Fed. Rep. of Germany

[21] Appl. No.: 429,175

[22] Filed: Oct. 30, 1989

[30] Foreign Application Priority Data

Nov. 29, 1988 [DE] Fed. Rep. of Germany ....... 3840204

[51] Int. Cl.$^5$ ............................................ C07C 319/02
[52] U.S. Cl. ................................................. 568/62
[58] Field of Search .................... 568/62; 549/472; 528/417

[56] References Cited

U.S. PATENT DOCUMENTS

| | | | |
|---|---|---|---|
| 3,431,239 | 3/1969 | Morris et al. | 568/62 |
| 3,824,197 | 7/1974 | Smith et al. | 525/410 |
| 4,259,474 | 3/1981 | Chakrabarti et al. | 528/388 |
| 4,355,185 | 10/1982 | Bergthaller et al. | 568/50 |

OTHER PUBLICATIONS

M. Movsumzade et al., Dokl. Akad. Nauk. Az. SSR (1978) 34(5), pp. 57–62.

*Primary Examiner*—Mary E. Ceperley
*Attorney, Agent, or Firm*—John H. Shurtleff

[57] ABSTRACT

Poly(1,4-butanediol-ω,ω'-mercaptans) have the general formula $$HS-(CH_2)_4-O-[(CH_2)_4-O]_n-(CH_2)_4-SH \qquad I$$

where n is from 1 to 150.

5 Claims, No Drawings

PROCESS FOR PREPARING A POLY(1,4-BUTANEDIOL-ω,ω'-BISMERCAPTAN)

The present invention relates to novel poly(1,4-butanediol-ω,ω'-bismercaptans) and to a process for preparing same.

Polytetrahydrofuran and derivatives thereof have become very interesting for use as intermediates for preparing polymers. Of particular interest here are those polytetrahydrofuran derivatives with terminal reactive groups such as polytetrahydrofuran-ω,ω'-diamines (U.S. Pat. No. 3,824,198), which make it possible to incorporate the polybutanediol chain in polymers.

The present invention provides novel polybutanediol derivatives which on account of their advantageous properties are suitable for example for use as regulators or crosslinkers in polymerizations for the preparation of plastics. These novel compounds have the general formula

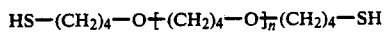

$$HS-(CH_2)_4-O+(CH_2)_4-O\overline{)_n}(CH_2)_4-SH \quad I$$

where n is from 1 to 150 and preferably from 2 to 70, in particular from 2 to 55.

Similar sulfur-containing polyethers are described in Example 3 of U.S. Pat. No. 3,824,197 where they are obtained by polymerization of tetrahydrofuran in the presence of trifluoromethanesulfonic anhydride and reaction of the resulting polytetrahydrofuran derivatives with hydrogen sulfide in pyridine. These sulfur-containing polytetrahydrofuran derivatives, however, have molecular weights of the order of 100,000. In addition, their sulfur content of the corresponding polybutanediols with terminal thiol groups.

The novel butanediol derivatives of the formula I are prepared for example by reacting polytetrahydrofuran derivatives of the general formula

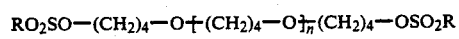

$$RO_2SO-(CH_2)_4-O+(CH_2)_4-O\overline{)_n}(CH_2)_4-OSO_2R \quad II$$

where R is alkyl of from 1 to 4 carbon atoms or aryl, and n is as defined above, with sulfur-donating compounds at up to 150° C., preferably at from 50° to 100° C.

In the polytetrahydrofuran derivatives of the formula II, R is alkyl of from 1 to 4 carbon atoms or aryl, such as phenyl or toluyl. The compounds of the formula II are thus for example poly(tetrahydrofuranbis-p-toluenesulfonate) as described in JP Patent 70/16,443 and the poly(tetrahydrofuranbisalkylsulfonate) as described in earlier German Patent Application P 38 34 265.0, which corresponds to copending U.S. application Ser. No. 408,702, filed Sep. 18, 1989.

The polytetrahydrofuran derivatives of the formula I are reacted with the sulfur-donating substances at up to 150° C., preferably at from 50° to 100° C. Sulfur-donating substances are for example hydrogen sulfide, sulfides, hydrogensulfides, thiosulfates, thiocyanates, xanthates, dithiocarbamates and thiourea. The sulfur-donating substances are advantageously used in stoichiometric amounts, but it is also possible to use excess amount, for example up to twice the amount. The reaction is preferably carried out in a solvent which under the reaction conditions does not react in an undesirable manner with the reactants. Suitable solvents are for example alcohols, such as ethanol, methanol or butanol, water, tetrahydrofuran, dioxane, dimethylformamide, dimethyl sulfoxide and N-methylpyrrolidone.

Particularly good results are obtained on reacting the polytetrahydrofuran derivatives of the formula II with thiourea. This particular version produces poly(1,4-butanediol-ω,ω'-bismercaptans) in particularly high selectivities.

EXAMPLE 1

In a 250 ml stirred apparatus equipped with a reflux condenser and a dropping funnel, 39 g (0.05 mol) of poly(tetrahydrofuranbismethanesulfonate) (see formula II where n = 6.7 and R = $CH_3$) are dissolved under nitrogen in 50 ml of ethanol (95 percent strength). 7.7 g of thiourea (0.1 mol) are added, and the mixture is heated at the boil for 3 hours. In the course of heating, the initially cloudy suspension turns clear. 6 g (0.15 mol) of NaOH in 60 ml of water are added dropwise, and the mixture is maintained at the boil for a further 2 hours and then cooled down to room temperature. It is acidified with 7.5 ml of 30 percent sulfuric acid (pH 1), and the top, organic layer is separated off. It is diluted with methyl tert-butyl ether (MTB) and dried over $Na_2SO_4$. Concentrating (60° C./50 mbar) leaves 28.7 g (87.5%) of poly(1,4butanediol-ω,ω'-mercaptan) of the formula I where n = 6.7 as a yellow oil in > 90% purity.

Analyses

Molecular weight (by osmometry): 700.

$^1$H-NMR (CDCl$_3$): δ =3.4 (m, polyether, CH$_2$) 2.56 (m, α-CH$_2$), 1.6 (m, polyether-CH$_2$), 1.35 (t, SH).

$^{13}$C-NMR (CDCl$_3$): δ =70.6 (polyether-C), 70.1 (δ-C to the SH group), 30.9 (β-C), 28.6 (γ-C), 26.7 (polyether-C), 244 (α-C to the SH group).

IR (film): 2939, 2856, 2796, 2565, 1483, 1447, 1436, 1368, 1208, 1114, 1017 cm$^{-1}$.

According to the above data, the dimeric by-product of the formula

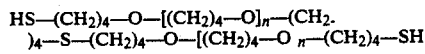

$$HS-(CH_2)_4-O-[(CH_2)_4-O]_n-(CH_2)_4-S-(CH_2)_4-O-[(CH_2)_4-O\overline{)_n}-(CH_2)_4-SH$$

formed in the course of the reaction is present in an amount of less than 5 mol % (≙ <10% by weight).

EXAMPLE 2

By the method of Example 1, 23.4 g (0.03 mol) of poly(tetrahydrofuranbismethanesulfonate) (see formula II where n = 6.7 and R = CH$_3$) and 14.9 g of sodium thiosulfate pentahydrate (0.06 mol) are dissolved in 100 ml of ethanol and 30 ml of water, and the mixture is refluxed for 6 hours. After cooling down to room temperature, 5 ml of concentrated hydrochloric acid and 35 ml of ethanol are added. The mixture is then refluxed for a further hour. After cooling down, 100 ml of water are added. It is extracted with MTB. Drying and concentrating the organic phase leaves 19.6 g (99.6%) of poly(1,4-butanediol-ω,ω'-bismercaptan) in a purity of about 54%. Analyses: molecular weight (by osmometry): 900. $^1$H-NMR (CDCH$_3$): δ =3.4 (m, polyether-CH$_2$), 2.7 (m, α-CH$_2$ of thioether), 2.56 (m, α, CH$_2$ of thiol), 1.6 (m, polyether-CH$_2$), 1.35 (t, SH).

The data indicate a proportion of tioether mentioned in Example 1 of about 30 mol % (≙ 54% by weight).

We claim:

1. A process for preparing a poly(1,4-butanediol-ω,ω'-bismercaptan), of the formula

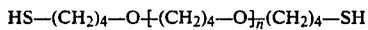  I where n is from 1 to 150, which comprises reacting a polytetrahydrofuran derivative of the formula

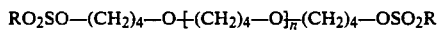  II where R is alkyl of from 1 to 4 carbon atoms or aryl and n is defined as above, with a sulfur-donating compound at a temperature up to 150° C.

2. A process as claimed in claim 1, wherein the polytetrahydrofuran derivative of the formula II is reacted with thiourea.

3. A process as claimed in claim 1, wherein the reaction temperature is from 50° to 100° C.

4. A process as claimed in claim 1, wherein the reaction is carried out in a solvent which will not react in an undesirable manner with the reactants.

5. A process as claimed in claim 4 wherein the solvent is selected from the group consisting of ethanol, methanol, butanol, water, tetrahydrofuran, dioxane, dimethylformamide, dimethylsulfoxide, and N-methylpyrrolidone.

* * * * *